United States Patent [19]
Schuresko

[11] 4,200,801
[45] Apr. 29, 1980

[54] PORTABLE SPOTTER FOR FLUORESCENT CONTAMINANTS ON SURFACES

[75] Inventor: Daniel D. Schuresko, Oak Ridge, Tenn.

[73] Assignee: The United States of America as represented by the United States Department of Energy, Washington, D.C.

[21] Appl. No.: 24,803

[22] Filed: Mar. 28, 1979

[51] Int. Cl.² .............................................. F21K 2/02
[52] U.S. Cl. .............................. 250/458; 250/461 R
[58] Field of Search .................. 250/253, 458, 461 R, 250/459

[56] References Cited
PUBLICATIONS

Barringer et al., Conference Proceedings of the Joint Conference on Sensing of Environmental Pollutants, New Orleans, La., Nov. 1977, pp. 778–781.
Measures et al., Joint Conference on Sensing of Environmental Pollutants, Palo Alto, Ca. Nov. 1971, AIAA Paper No. 71-1121.
Technical Bulletin, Sick Optik–Elektronik, Inc. Stillwater, Minn., LUT/Lun Luminescence Scanner.

Primary Examiner—Davis L. Willis
Attorney, Agent, or Firm—R. V. Lupo; Stephen D. Hamel; David E. Breeden

[57] ABSTRACT

A portable fluorescence-based spotter for polynuclear aromatic hydrocarbon contamination on personnel and work area surfaces under ambient lighting conditions is provided. This instrument employs beam modulation and phase sensitive detection for discriminating between fluorescence from organic materials from reflected background light and inorganic fluorescent material. The device uses excitation and emission filters to provide differentiation between classes of aromatic organic compounds. Certain inorganic fluorescent materials, including heavy metal compounds, may also be distinguished from the organic compounds, despite both having similar optical properties.

6 Claims, 4 Drawing Figures

PORTABLE SPOTTER FOR FLUORESCENT CONTAMINANTS ON SURFACES

BACKGROUND OF THE INVENTION

This invention was made during the course of, or under, a contract with the U.S. Department of Energy.

This invention relates generally to the art of photoelectric instruments for measuring fluorescence and more specifically to a fluorescence spotter for detecting organic fluorescent substances in the presence of inorganic fluorescent substances with similar optical properties, and vice versa.

Survey monitoring in coal conversion work areas for surface contamination caused by spills, leakage or contact transfer of material containing carcinogenic polynuclear aromatic hydrocarbon compounds or mutagenic acridines is essential for the health and safety of personnel. For this kind of survey monitoring, a portable direct reading instrument, similar in function to the familiar radiological survey devices is needed. Most of the polynuclear aromatic hydrocarbon compounds (PNA), whether in the form of liquid or dried spills, can be made to fluoresce in the presence of ultaviolet light. In order to take advantage of this property of PNAs in coal-conversion work areas, there is a more specific need for an instrument which is capable of functioning during actual plant operation in variable working environments. The instrument must be able to detect spilled material on various work surfaces including machinery, plumbing, construction materials and on personnel and clothing. The instrument must be capable of making these measurements in the presence of ordinary (bright) illumination from room lighting and sunlight while also being easily and reliably operated by all plant personnel.

In the art of fluorometric-based instruments for detecting materials which fluoresce under the influence of exposure to light in the ultraviolet range, primarily, modulation of the excitation beam source has been employed in order to detect the low-level fluorescence of materials in the presence of interference by continuous light such as ordinary sunlight, etc. However, these instruments have not dealt with the problems encountered by AC lighting sources, i.e., 120 cycle indoor lighting, which introduce additional problems in discriminating low-level fluoresence in the presence of the relatively high-level AC lighting. Thus, in order to provide an instrument which is operable within a coal conversion facility and which will detect fluorescence of certain PNA materials in submicrogram quantities, one must deal with the problem of interfering AC light sources.

Additionally, in order to monitor or detect these organic materials at the low levels which have been determined to be hazardous to the health of personnel working in the area, there is a need for an instrument which will discriminate the fluorescence of the hazardous organic materials from the fluorescence of various inorganic materials such as those pigments commonly used in paints. These materials may fluoresce at wavelengths within the same general band as that of the organic materials which are to be detected and interfere with the measurement of toxic organic materials.

Thus, it will be seen that there is a need for an instrument which not only will operate to detect various classes of polynuclear aromatic hydrocarbon compounds in a coal-conversion plant, for example, but which, in addition, will detect these materials in the presence of intense background room lighting and in the presence of other fluorescent materials to ensure low-level contamination detection while providing some quantitative measure of the detected levels.

SUMMARY OF THE INVENTION

In view of the above need, it is a primary object of this invention to provide an instrument which will detect polynuclear aromatic substances which fluoresce when illuminated by an ultraviolet light source in the presence of ordinary room light and in the presence of other materials which also fluoresce within the same wavelength band as the class of materials being detected.

Another object of this invention is to provide an instrument as set forth in the above object wherein the fluorescence of selected classes of materials may be detected in the presence of alternating current lighting sources by a selected modulation of the light excitation beam which induces fluorescence in the material at frequencies which allow a detecting demodulation circuit to discriminate between the fluorescence and the alternating background light.

Yet another object of this invention is to provide an instrument as set forth in the above objects which further includes means for detecting phase shifts in the detected fluorescence (from a reference signal at the corresponding modulation frequency) in order to distinguish between the quantity of light from fluorescence of the selected class of organic materials and the quantity of light detected from the fluorescence of inorganic materials to provide a quantitative detection of either of the materials in the presence of the other.

Other objects and many of the attendent advantages of the present invention will be obvious from the following detailed description taken in conjunction with the drawings.

DETAILED DESCRIPTION

Figure 1:
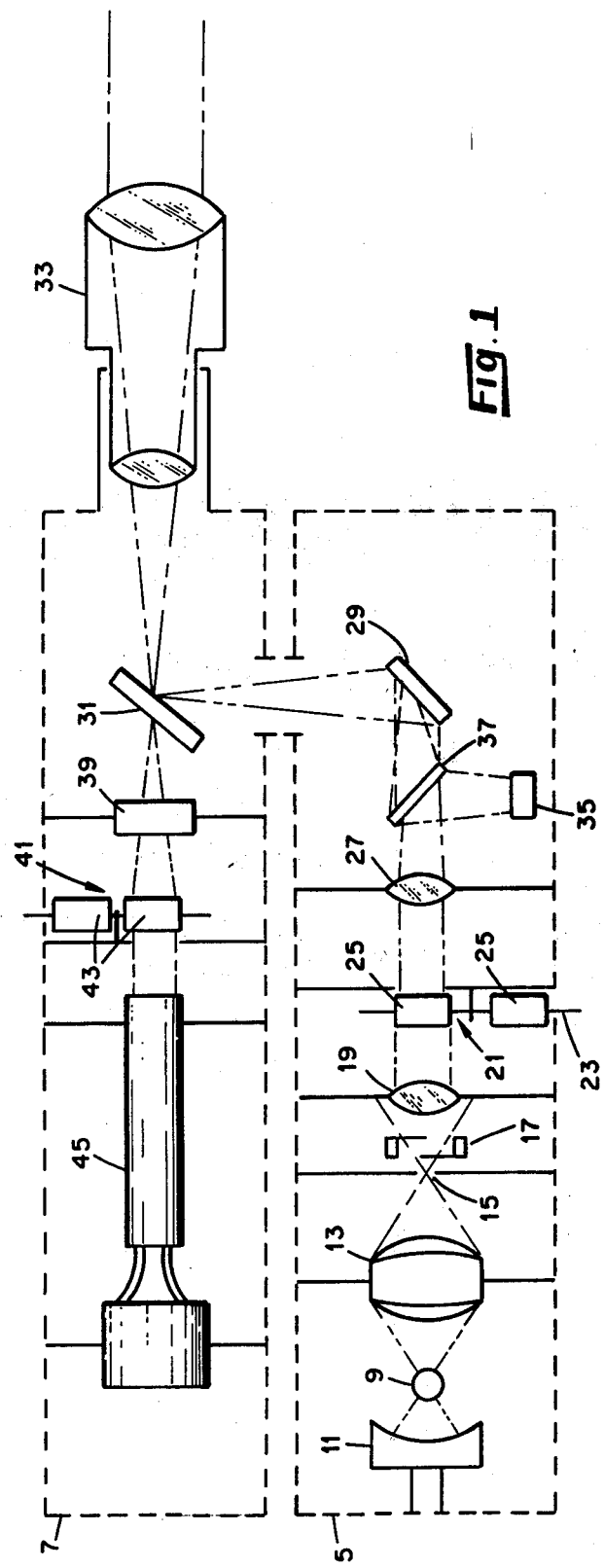
FIG. 1 is a schematic diagram illustrating the optical portion of a fluorescence contaminant spotter according to the present invention.

The spotter consists of a detector head as shown schematically in FIG. 1 and an electronic unit which may be separated from the detector head portion to provide a portable instrument in which the electronic unit, including a battery pack, may be carried by a shoulder strap. The detector head may be embodied in a housing having a pistol-grip arrangement, for example, for conveniently aiming the exciting ultraviolet light beam from the detector onto the area to be surveyed.

The detector head, shown schematically in FIG. 1, consists of two compartments. The lower compartment 5 includes a light source and excitation filtering to produce a monochromatic beam of ultraviolet visible fluorescence-exciting light. The upper compartment 7 includes the fluorescence emission filtering and detecting portion for detecting the fluorescence emitted from the illuminated surface. The fluorescence light is discriminated from background light by a beam modulation and phase sensitive detection technique. A single lens reflection/transmission system, which incorporates a dichromatic beam splitter, ensures proper overlap of the transmitter's field of illumination and the receiver's field of view.

Referring now to the lower portion of the detector head, light from a high-pressure ultraviolet lamp 9 is directed by means of a reflector 11 through a condenser lens 13 and a pinhole 15 whereupon it is modulated by a tuning-fork type chopper 17. The beam chopper aids in discriminating against background room light whose frequency is 120 Hz plus harmonics. The beam is modulated at 1000 Hz which is well separated from the room light frequency and its harmonics. After being modulated the beam passes through a collimating lens 19 and then through a selected one of a multiple selectable filter arrangement 21 where the excitation band corresponding to a desired class of fluorogenic materials is selected. The particular type of filters used in the filter selector arrangement may take various forms, however, the preferred type of filter is a fixed bandpass glass absorbance filter. The filters may be arranged for selection in various ways also, such as mounting the filters on slides which may be moved into place in the beam, or the filters may be placed on a marked thumb wheel 23 wherein the individual filters 25 may be selectively rotated into place in the beam as shown in FIG. 1. For polynuclear aromatic materials (PNAs) the excitation filter 25 should have a light wavelength bandpass of 350 to approximately 380 nanometers. For organic compounds such as solvents like benzene, toluene, xylene and simple phenols, the bandpass should be between about 230–280 nanometers.

The light passing through the selected filter is then focused by means of a focusing lens 27 and a reflector 29 onto a dichromatic beam splitter 31 in the upper compartment 7. The beam is then output via a telephoto objective 33. A portion of the excitation beam is routed to a reference photodiode 35 by means of a beam splitter 37. The beam splitter 37 reflects approximately 4% of the beam onto the photodiode 35. The photodiode 35 provides a signal which is used to offset beam splitter and telephoto background fluorescence and to correct the fluctuations in the intensity of the excitation beam from the lamp 9.

The receiver portion of the detector head views the area illuminated by the excitation beam and detects all incoming light in the selected emission bandwidth. The fluorescence emission of the material being illuminated and background light is collected by the telephoto objective lens 33 and passes through the dichromatic beam splitter 31. The beam splitter 31 passes the longer wavelengths of the fluorescence being detected but not the shorter wavelength of the illuminating ultraviolet light. The emission beam passes through a barrier filter 39 which rejects all frequencies above a selected cutoff frequency according to the particular barrier filter selected to reject backscatter and reflections of the excitation beam. The beam then passes through a selected emission filter in a selectable emission filter arrangement 41 similar to the filter arrangement 21. A particular emission filter 43 in the selector arrangement is selected to correspond with the particular class of compounds to be surveyed. For PNAs the particular filter 43 should have a transmission bandwidth of between about 430–600 nanometers. For the organic solvents the filter bandwidth should be between about 310–360 nanometers. The filtered fluorescence emission is then detected by means of a photomultiplier tube (PMT) 45 which generates a current proportional to the incident light intensity.

Figure 2:
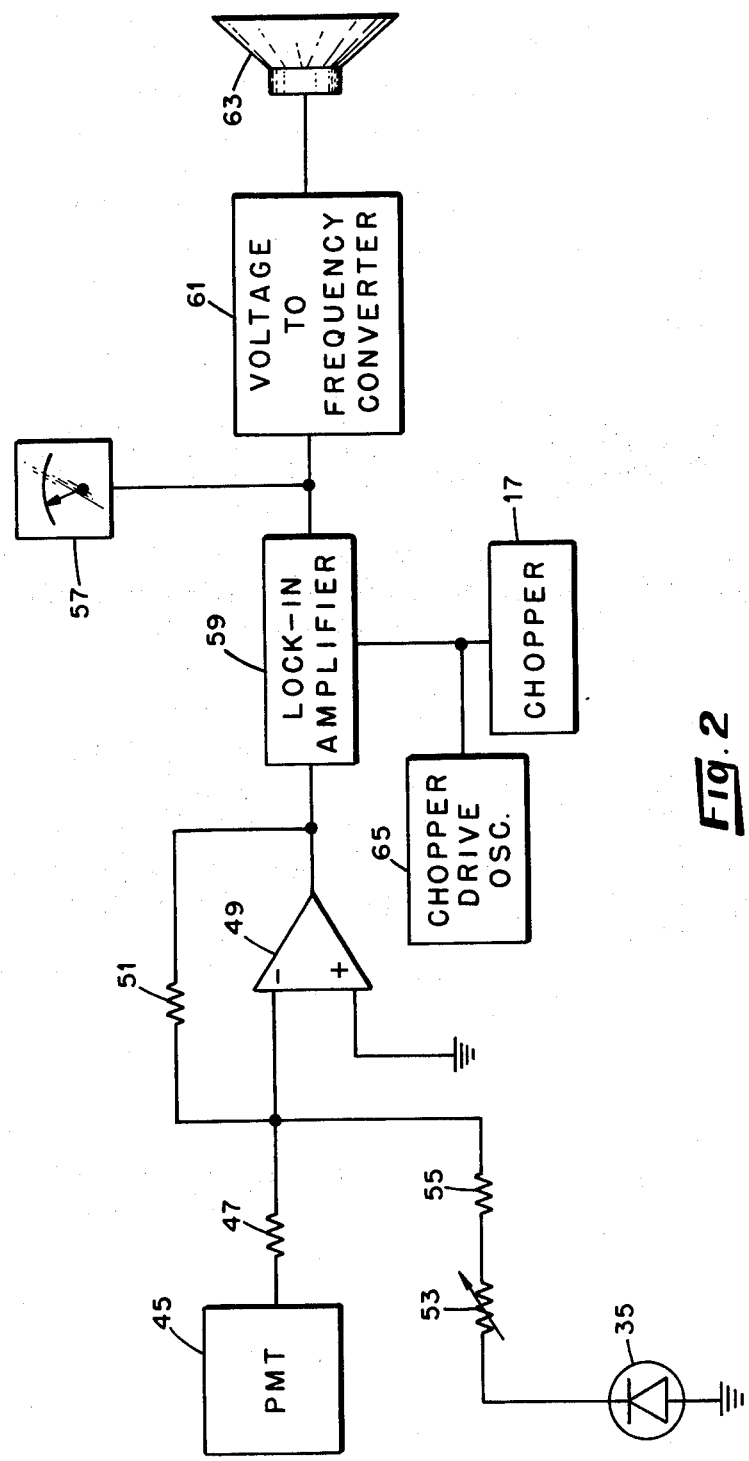
FIG. 2 is a schematic block diagram of the electronic portion of the spotter including the photomultiplier, chopper and photodiode shown in FIG. 1.

Referring now to FIG. 2 wherein there is shown the electronic components in block form, the photomultiplier tube 45 has its output connected through a resistor 47 to the inverting input of an operational amplifier 49. Amplifier 49 is connected as a summing amplifier with negative feedback control by means of resistor 51 connected between the output of amplifier 49 and the noninverting input. The photodiode 35 has its anode connected to ground and its cathode lead connected through a variable resistor 53 and a second summing input resistor 55 to the inverting input of amplifier 49. To null the instrument prior to a measurement operation, the telephoto lens 33 is covered so that no fluorescence emission is received and the resistor 53 is adjusted for a null condition on the output meter 57. The output of amplifier 49 is connected to the signal input of a lock-in amplifier 59. The lock-in amplifier 59 output is connected to a voltage-to-frequency converter 61 and to the meter 57. The output of the voltage-to-frequency converter 61 is connected to a speaker 63 which sounds an audible alarm when fluorescence is detected. The reference input of the lock-in amplifier 59 is connected to the output of the chopper drive oscillator 65. The oscillator 65 drives the chopper 17 at 1 kHz which modulates the illuminating ultraviolet beam.

Various lock-in amplifier arrangements may be used for the phase sensitive detection of the fluorescence emission signal to eliminate fluorescence from inorganics when measuring fluorescence from organics, or vice versa, as will be described. For example, if instrument portability is not the problem, a commercially available lock-in amplifier, such as the Ithaco Corp., Model Dynatrac 3 (Ithaca, N.Y.), may be used. This unit extracts the 1 kHz modulated fluorescence signal from the background light by means of phase sensitive demodulation. Since the output of the chopper drive oscillator is 1 kHz which drives the chopper 17, this signal applied to the reference input of the lock-in amplifier keys the amplifier to extract the 1 kHz fluorescence signal. The phase of the reference signal may be arbitrarily adjusted so that it is exactly in phase with the modulated fluorescence emission signal from the photomultiplier tube 45 for a given sample. For organic compounds, the fluorescence signal phase shift compared to the modulated ultraviolet (U.V.) intensity is negligible. However, the reference phase may be adjusted slightly to peak the meter 57 giving the maximum fluorescent signal for organic compounds thus cancelling out any signal phase shifts due to the electronics. The Dynatrac 3 lock-in amplifier also employs a 90° phase shift capability for the reference signal which extracts the component of the input signal due to inorganic fluorescence. The shift is approximately a 90° phase shift due to the difference in the fluorescence lifetime of fluorogenic inorganic materials as compared to fluorogenic organic materials at the 1 kHz modulation frequency. Thus, the selected outputs are essentially the A cosine $\theta$ component of the fluorescent signal which corresponds to organic material fluorescence and a quadrature component output which is essentially an A sine $\theta$ component of the emission signal which corresponds to inorganic fluorescent materials, where θ, the phase shift between the organic or fast fluorescence and the reference signal, is normally adjusted to zero.

Figure 3:
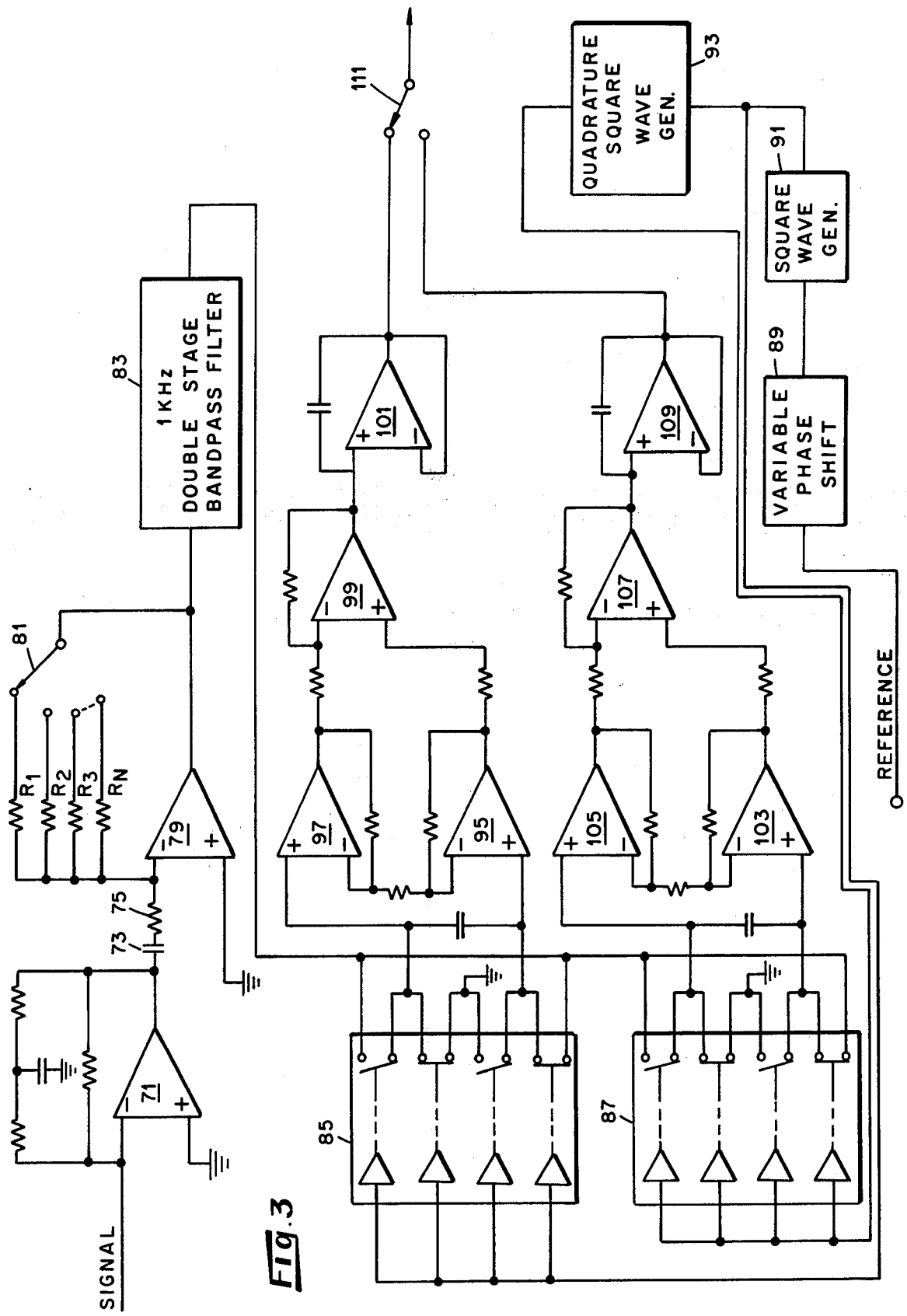
FIG. 3 is a schematic diagram of a specific lock-in amplifier circuit shown in block form in FIG. 2.

In a portable instrumentation package the use of a Dynatrac 3 lock-in amplifier is not practical. Therefore, a lock-in amplifier design, which is shown in FIG. 3, is used to accomplish the same signal demodulation, but with a much simpler circuit which may be miniaturized to enhance portability of the unit. As shown in FIG. 3, the current signal from photomultiplier 45 is applied to the input of a current-to-voltage converter 71. The converter 71 also acts as a partial low frequency and DC filter. The output of the converter 71 is connected through a coupling capacitor 73 and a gain control resistor 75 to the input of a gain selectable amplifier 79. The output of amplifier 79 is selectively connected by means of a switch 81 to a plurality of gain control resistors R-1 through $R_n$ which are provided to select the instrument sensitivity in a fluorescence measurement. The output of amplifier 79 is connected to the input of a 1 kHz double-stage bandpass filter which removes the modulated fluorescence signal from the background light signal including that of AC light in an ordinary room lighting. The output of the filter 83 is connected to a pair of electronic switches 85 and 87. The switches 85 and 87 are controlled by signals developed from the reference signal which is the ouput of the oscillator 65, FIG. 2. The reference signal is applied to the input of a variable phase shift circuit 89 whose output is connected to a square wave generator 91. The output of square wave generator 91 is connected to the input of a quadrature square wave generator 93. Generator 93 generates a square wave which is shifted 90° in phase from that of the square wave generator 91. The output of generator 91 is connected to control the 4 poles of the electronic switch 85 and the output of quadrature square wave generator 93 is connected to control the 4 poles of electronic switch 87. The phase sensitive detection of the in-phase fluorescent signal corresponding to an organic compound is controlled by the switching operation of the 4 poles of electronic switch 85. The quadrature component of the fluorescent signal, corresponding to any inorganic fluorescence which appears as a 90° phase shifted signal, is extracted by means of electronic switch 87 controlled by the quadrature square wave generator 93. The in-phase component of the signal from filter 83 is applied to an instrumentation amplifier section consisting of operational amplifiers 95, 97 and 99. When the output of square wave generator 91 controlling the 4 poles of the switch 85 is in phase with the organic component of the fluorescence, the output of amplifier 99 is a positive voltage proportional to the level of in-phase fluorescence detected by the instrument. This signal at the output of amplifier 99 is connected to an integrator 101 which produces a DC output indicative of the fluorescence measured from an organic material.

Similarly, the quadrature component of the fluorescent signal is extracted by means of an instrument amplifier package including operational amplifiers 103, 105 and 107. The output of amplifier 107 corresponds to the component of the signal from filter 83 which is due to the time shifted fluorescence of the inorganic portion of the fluorescent signal extracted by means of the quadrature reference wave from generator 93. The output of amplifier 107 is fed to an integrator 109 whose output is a DC signal indicative of the fluorescence emission measured of any inorganic materials present. A selector switch 111 is provided on the instrumentation package which allows the operator to select either the organic or inorganic component of the fluorescence signal.

Figure 4:
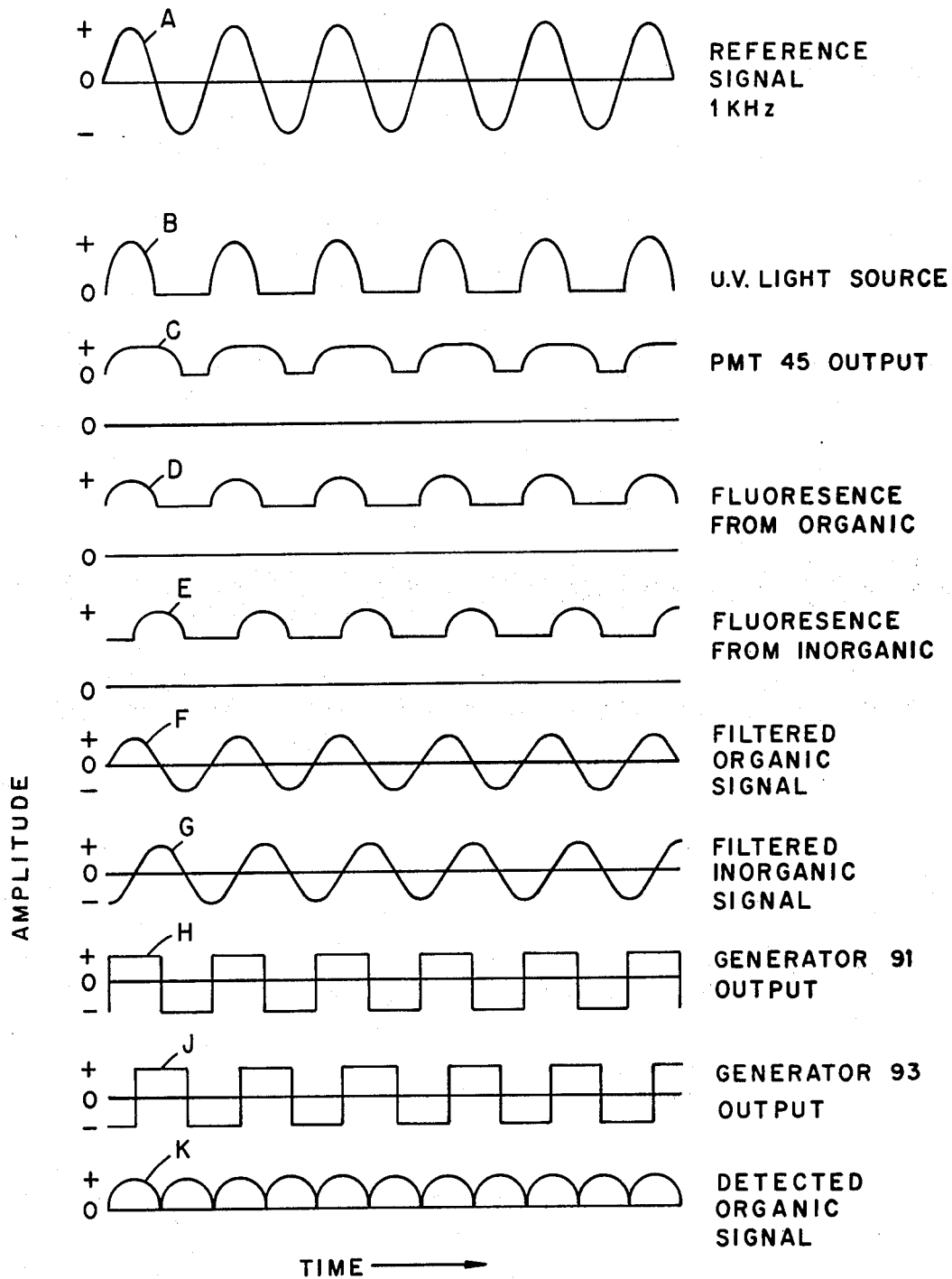
FIG. 4 is a graphic illustration of the various waveforms at various points in the detecting activity circuitry which have been simplified to illustrate clearly the operation of the invention.

Referring now to FIG. 4 in conjunction with FIGS. 2 and 3, the operation of the system will be described. Assuming the appropriate filters in the detector head (FIG. 1) have been selected for the class of organic materials to be detected, the ultraviolet light source is turned on and the meter 57 is nulled with the lens covered by adjusting the potentiometer 53. This eliminates errors introduced due to fluorescence in the optics which appear as organic fluorescence signals. The instrument may then be calibrated by placing a pure organic sample of the selected class in the beam. An accurate calibration must also consider the distance of the sample from the detector head lens. The sensitivity is selected by proper gain selection through the selector switch 81.

Once the preliminary operations are completed, a survey of a contaminated area may be made. In areas where fluorescence is detected, accurate measurements of the fluorescence of the detected material may be made by holding the detector head lens at the calibrated distance from the spill. The meter may be calibrated to read directly in milligram quantities. Typically the sensitivity for health physics surveys would be in the range of from $10^{-4}$ to 1 milligrams.

As shown in FIG. 4, the U.V. source is modulated by means of a 1 kHz signal (A) applied to the chopper 17. The U.V. light excites the material to be detected by means of pulses of light with a 1 kHz repetition rate as shown by signal trace B. When a spill is "sighted,38 the output of the photomultiplier tube 45 will include the emitted fluorescence signal sitting atop a much larger magnitude signal due to background light as shown by trace C. It should be pointed out that signal trace C represents, greatly simplified to aid in describing the detection process, a rather complicated waveform which in actual practice includes some noise at 1 kHz but at a random phase. Trace C also assumes a constant background light source such as sunlight. When the instrument is used indoors under artificial lighting at 120 cycles the fluorescence signal sits atop a background signal which varies at 120 Hz. However, it will be obvious from the following discussion how this variation in background light will be removed during the detection process. Further, in trace C it is assumed that there is a component of detected fluorescence due to inorganic materials to show how the instrument can distinguish between the two signals.

The "prompt" component of the fluorescence signal in trace C is typical of organic materials whose fluorescence lifetimes range from 1–100 nanoseconds; the "delayed" component arises from the fluorescence of inorganic materials, whose fluorescence lifetimes range from 1–1000 microseconds. Further, discussion of the differences in fluorescence lifetimes of organic and inorganic materials may be found in the following references:

1. Birks, J.B., and Munro, I. H., *Process in Reaction Kinetics*, Vol. 4, p. 239.
2. Curie, Daniel, *Luminescence in Crystals*, John Wiley & Sons, N.Y., N.Y. (1963).

The delay in fluorescence of the inorganic material appears as a phase shifted signal if the organic and inorganic fluorescence signal components were separated from the compound signal trace C as illustrated by traces D and E. The organic signal component D will be essentially in phase with the reference or modulating signal while the inorganic signal is shifted by approximately 90°. Thus, by phase sensitive detection the fluorescence intensity of an organic material in the presence of fluorogenic inorganic materials at the same fluorescence wavelength may be distinguished, and vice versa.

As pointed out above, this measurement may be made by commercially available lock-in amplifiers. However, for a portable instrument the circuit of FIG. 3 is preferred in which the same function is accomplished in a different manner. Here the PMT 45 signal is applied to the input of amplifier 71 which reduces the DC component of the signal. The AC component of the signal is coupled through capacitor 73 to the input of amplifier 79 which amplifies the signal according to the selected gain. This signal is then filtered by the 1 kHz centered bandpass filter 83 which passes all components of the signal within the 1 kHz band and rejects all others, such as the 120 Hz background room light. Although the actual signal from filter 83 is a compound signal of both the organic and inorganic fluorescence signals and any other detected light at 1 kHz, the idealized signal traces F and G represent the filtered organic and inorganic components of the total signal which is applied to the electronic switches 85 and 87. The switches 85 and 87 are operated by the reference signals H and J, respectively, so that when the signals are positive the poles of the switches are in the states as shown in FIG. 3 and when the signals go negative each pole is reversed. Reference signal H, referred to as the in-phase signal, controls the extraction of the organic signal F. As shown during the time signal H is positive, the filtered signal is applied to the positive input of operational amplifier 95 which applies the signal uninverted to the positive input of operational amplifier 99 whose output is positive. When signal H goes negative the filtered signal is switched to the positive input of operational amplifier 97. But at this point the component of the signal due to organic fluorescence, signal F, is negative. The output of amplifier 97 is negative. When this signal is applied to the negative, or inverting, input of amplifier 99, its output is again positive. The signal is as shown by trace K in the idealized case. This signal is integrated by integrator 101 over a number of cycles producing a positive DC signal at the output of integrator 101 which is indicative of the organic fluorescence intensity only.

As pointed out above, both components of the filtered signal are applied to the switches 85 and 87. However, the signal component G due to inorganic fluorescence is averaged out of the signal at the output of integrator 101 due to the quadrature phase shift of signal relative to signal F. When the switching takes place only half of the positive or negative portion of signal G goes through the amplifiers 95 and 99 uninverted. The other half passes through amplifiers 97 and 99 but is inverted and thus is averaged out of the DC signal at the output of integrator 101 leaving only the in-phase signal component from the detected fluorogenic organic material.

In the same manner switch 87, operational amplifiers 103, 105 and 107 and integrator 109 detect the quadrature component of the filter 83 output, signal G, to produce a separate DC signal indicative of the fluorogenic inorganic material being detected. Either signal may be selectively routed to the meter 57 and speaker 63 by means of selector switch 111.

In a typical survey operation, the telephoto lens 33 is adjusted so as to focus the excitation beam at a distance of 40 cm from the spotter (the cross sectional area of the beam at focus is approximately 4 $cm^2$), which results in roughly distance independent fluorescence measurements for distances ranging from 0–80 cm. As pointed out above, a more accurate measurement is made at the calibrated distance.

The spotter has been laboratory tested with a variety of liquid samples and with films and smears of coal conversion oils on various construction materials. Table 1 lists the sensitivity of the spotter to various solvent refined coal (SRC) process liquids and other process liquids. 1–20 micron thick films of these materials on microscope slides with cover slips were used as samples in these measurements. The transmission filter used was a bandpass absorption-type filter with a transmission bandwidth between 330 and 370 nm. The fluorescence emission filter used was a bandpass interference-type filter with a transmission bandwidth between 510 and 530 nm. The variation in sensitivity to the different coal liquefaction or oil shale products generally reflects the different PNA content of each; for some substances (e.g., Oak Ridge National Laboratory (ORNL) hydrocarbonization oil), the sensitivity also apparently depends upon the relative asphaltene vs light oil content of the material. These data are actually upper limits on sensitivity since they were computed by normalizing the measured fluorescence from milligram amounts of each oil by the observed detector noise and by the amount of material observed. Milligram level smears of ORNL hydrocarbonization oil and COED syncrude on floor tile and on metallic surfaces have also been detected in a less quantitative fashion.

TABLE 1

SENSITIVITY TO VARIOUS SUBSTANCES
(EXCITATION = 350 nm, EMISSION = 520 nm,
DISTANCE = 60 cm)

| SAMPLE | SENSITIVITY (MICROGRAMS) |
|---|---|
| SRC-I RECYCLE SOLVENT | 27 |
| SRC-I WASH SOLVENT | 129 |
| SRC-I PROCESS SOLVENT | 34 |
| SRC-I LIGHT ORGANIC LIQUID (RAW) | 884 |
| SRC-II FUEL OIL BLEND | 17 |
| CENTRIFUGED SHALE OIL (PROCESS I) | 26 |
| HYDROTREATED COAL DISTILLATE | 38 |
| PRODUCT DISTILLATE ($ZnCl_2$) | 11 |
| COED SYNCRUDE | 20 |
| ORNL HYDROCARBONIZATION OIL (HC-12) | 790 |

Table 2 lists the spotter's sensitivity to solutions containing PNAs or acridines, including some hydrocarbonization waste waters and to solutions containing pure compounds. The spotter is sensitive to microgram amounts of pure compounds (perylene) in dilute solution.

TABLE 2

SENSITIVITY TO VARIOUS SUBSTANCES

| SAMPLE | SENSITIVITY (MILLIGRAMS) | DISTANCE (cm) |
|---|---|---|
| HC-10 SCRUBBER $H_2O$ | 1.0 | 22 |
| HC-8 BIOREACTOR FEED | 10.0 | 22 |
| W-41 BIOREACTOR EFFLUENT | 250.0 | 22 |

TABLE 2-continued

SENSITIVITY TO VARIOUS SUBSTANCES

| SAMPLE | SENSITIVITY (MILLIGRAMS) | DISTANCE (cm) |
|---|---|---|
| UNH UO$_2$(NO$_3$)$_2$ 6H$_2$O | 1.0 | 27 |
| PERYLENE | .001 | 82 |

Coal liquefaction products may contain sufficient amounts of some compounds which quench the fluorescence of PNAs and thus interfere with fluorometric monitoring techniques. Two classes of aromatic compounds which are abundant in coal conversion products are phenols and acridines. Tests have been conducted for phenol interference by adding large excesses of phenol to solutions containing perylene. As expected from the fact that there is no overlap between the optical absorption of phenol and the fluorescence emission of PNAs, it was found that phenols do not interfere with fluorometric PNA determinations. However, heteroatom aromatic compounds such as acridines which are abundant in oils having a high asphaltene content, do apparently affect PNA fluorescence. The optical absorption of many acridines does overlap the emission from PNAs, resulting in a shift of the fluorescence to longer wavelengths and a decrease in its intensity. However, normal PNA fluorescence of materials such as ORNL hydrocarbonization oil is observed upon 5-fold dilution of the oil with aliphatic solvents or oils.

The spotter provides the capability for discrimination among classes of organic contaminants, such as PNAs and BTXs (benzene, toluene, xylene), by selection of optimal excitation and emission wave-lengths with optical filters. The spotter also discriminates the fluorescence of uranyl nitrate (UNH) from the fluorescence of organic compounds, despite both having similar optical properties, due to the fact that the fluorescence lifetime of uranyl nitrate is comparable to the 1 msec beam modulation period. This results in a non-zero phase shift in the fluorescence signal from uranyl nitrate samples which can be discriminated electronically with the phase-sensitive demodulation technique. The spotter is sensitive to 1 mgm amounts of UNH and may be further useful in nuclear fuel and waste handling facilities to locate spills or leakage of UNH containing liquids which are difficult to detect due to the short range of their emitted alpha radiation. Beryllium compounds may also be detectable.

Thus, it will be seen that a very useful instrument for spotting fluorogenic organic compounds, especially hazardous compounds in coal conversion facilities, in the presence of fluorogenic inorganic materials has been provided. The characteristics of the prototype spotter which are important to its function as a survey device are:

1. Its high sensitivity, due to the strong native fluorescence of PNAs.
2. Its ability to operate in either illuminated or darkened work areas.
3. Its ability to yield a semiquantitative measurement of the amount of spilled material at variable spotter-to-surface distances.
4. Its ability to detect spills remotely at distances from one-half to four feet.

What is claimed is:

1. A fluorescence sensitive spotter for detecting fluorescent contaminant materials on a surface comprising:
   a fluorescence exciting light source means for directing a beam of said fluorescence exciting light onto said surface and material;
   means including a reference signal generator for modulating said light source beam at the frequency of said reference signal which differs substantially from frequency of variation of extraneous background light reflected from said surface;
   light detecting means for detecting the fluorescence emission induced by said modulated light source and background light from said surface and generating an electrical signal in response thereto; and
   phase sensitive detection means responsive to the phase relationship between the detected fluorescence signals from said materials and said reference signal for separately detecting fluorescence signals from different types of said materials each in the presence of the other which fluoresce at substantially the same fluorescence light wavelength but differ in fluorescence lifetimes.

2. The fluorescence sensitive spotter as set forth in claim 1 further including optical filtering means for selectively detecting different classes of said types of materials according to differing fluorescence excitation and emission wavelengths including a first plurality of separately selectable filters for location in said excitation beam to select a predetermined frequency bandwidth of said excitation light beam corresponding to the bandwidth which produces fluorescence in a selected class of said types of materials to be detected by said spotter and a second plurality of separately selectable filters for location in the detected light path corresponding to the emission bandwidth of fluorescence light detected from said selected class of said types of materials.

3. The fluorescence sensitive spotter as set forth in claim 2, wherein said different types of said materials include fluorogenic organic materials and fluorogenic inorganic materials and wherein said phase sensitive detection means includes means for adjusting the phase shift of said reference signal applied thereto for selective separate synchronous detection of the magnitude of the component of the fluorescence signal from said organic material and the magnitude of the component of the fluorescence signal from said inorganic material.

4. The fluorescence sensitive spotter as set forth in claim 3 wherein said light detection means includes a photomultiplier tube disposed to receive the filtered fluorescence emission and background light from said surfaces.

5. The fluorescence sensitive spotter as set forth in claim 4 wherein said modulation means and said phase sensitive detection means further include a beam chopper located in said excitation beam path and operatively connected to the output of said reference signal generator for chopping said excitation light beam at the reference signal frequency, a lock-in amplifier having a signal input coupled to the output of said photomultiplier tube and a reference signal input connected to receive said reference signal from said reference signal generator and an output circuit means for separately selecting and applying to an output terminal thereof a first output signal corresponding to the magnitude of fluorescence from the selected a class of organic materials detected on said surface and a second output signal corresponding to the magnitude of fluorescence from the selected class of inorganic materials detected on said surface, and indicator means connected to said output terminal of said lock-in amplifier for indicating the magnitude of the selected signal from said amplifier corresponding to the detected fluorescence.

6. The fluorescence sensitive spotter as set forth in claim 5 further including optical means including a telephoto lens for focusing said excitation beam on said surface through said telephoto lens and receiving said light from said material and said surface through said telephoto lens and focusing said received light onto the light sensitive surface of said photomultiplier tube.

* * * * *